(12) United States Patent (10) Patent No.: US 12,589,153 B2
Al-Rashid et al. (45) Date of Patent: Mar. 31, 2026

(54) POLYURETHANE EXCIPIENT

(71) Applicant: DSM IP Assets B.V., Heerlen (NL)

(72) Inventors: Jennifer Al-Rashid, Exton, PA (US); Jacob Riffey, Exton, PA (US); John Andrew Zupancich, Exton, PA (US)

(73) Assignee: DSM IP ASSETS B.V., Maastricht (NL)

( * ) Notice: Subject to any disclaimer, the term of this patent is extended or adjusted under 35 U.S.C. 154(b) by 0 days.

(21) Appl. No.: 18/984,821

(22) Filed: Dec. 17, 2024

(65) Prior Publication Data

US 2025/0114459 A1      Apr. 10, 2025

Related U.S. Application Data

(62) Division of application No. 17/275,729, filed as application No. PCT/US2019/051289 on Sep. 16, 2019, now Pat. No. 12,214,041.

(60) Provisional application No. 62/732,073, filed on Sep. 17, 2018.

(30) Foreign Application Priority Data

Sep. 28, 2018      (EP) .................................... 18197763

(51) Int. Cl.
| | |
|---|---|
| *A61K 47/34* | (2017.01) |
| *A61K 9/00* | (2006.01) |
| *A61K 47/32* | (2006.01) |
| *C08G 18/08* | (2006.01) |
| *C08G 18/12* | (2006.01) |
| *C08G 18/32* | (2006.01) |
| *C08G 18/40* | (2006.01) |
| *C08G 18/44* | (2006.01) |
| *C08G 18/48* | (2006.01) |
| *C08G 18/73* | (2006.01) |
| *C08G 18/75* | (2006.01) |

(52) U.S. Cl.
CPC ............ *A61K 47/34* (2013.01); *A61K 9/0036* (2013.01); *A61K 47/32* (2013.01); *C08G 18/0895* (2013.01); *C08G 18/12* (2013.01); *C08G 18/3206* (2013.01); *C08G 18/4018* (2013.01); *C08G 18/44* (2013.01); *C08G*

*18/4833* (2013.01); *C08G 18/73* (2013.01); *C08G 18/758* (2013.01)

(58) Field of Classification Search
CPC ...... A61K 47/34; A61K 9/0036; A61K 47/32; C08G 18/12; C08G 18/4018; C08G 18/44; C08G 18/4833; C08G 18/73; C08G 18/758; C08G 18/0895; C08G 18/3206
See application file for complete search history.

(56) References Cited

U.S. PATENT DOCUMENTS

| | | | |
|---|---|---|---|
| 5,428,123 A | 6/1995 | Ward et al. | |
| 5,589,563 A | 12/1996 | Ward et al. | |
| 12,214,041 B2 * | 2/2025 | Al-Rashid | A61K 47/32 |
| 2009/0252699 A1 | 10/2009 | Kocher | |
| 2013/0196003 A1 | 8/2013 | Bluecher | |
| 2021/0163668 A1 | 6/2021 | Bokel | |

FOREIGN PATENT DOCUMENTS

| | | |
|---|---|---|
| WO | 2008003932 | 1/2008 |
| WO | 2012/066000 | 5/2012 |

OTHER PUBLICATIONS

International Search Rep[ort and Written Opinion dated Feb. 12, 2019.

* cited by examiner

*Primary Examiner* — Rabon A Sergent
(74) *Attorney, Agent, or Firm* — NIXON & VANDERHYE P.C.

(57) ABSTRACT

In an embodiment, a polyurethane comprises the residues of i. an aliphatic diisocyanate, ii. an aliphatic diol comprising a poly(ethylene oxide) moiety, iii. an aliphatic diol comprising a polycarbonate moiety, and iv. a chain extender, wherein the polyurethane has a melting temperature of 140° C. or less and has a weight average molecular weight of from 100,000 to 500,000 g/mol. In an embodiment, the polyurethane is substantially devoid of catalyst. In an embodiment, the polyurethane is formed by reactive extrusion. In an embodiment, a medical device comprises the polyurethane and a bioactive agent. The medical devices, methods, and polyurethanes may exhibit benefits in end-product biostability, drug release profile, health and safety, and processing speed or reproducibility.

18 Claims, No Drawings

POLYURETHANE EXCIPIENT

CROSS-REFERENCE TO RELATED APPLICATIONS

This application is a divisional of U.S. application Ser. No. 17/275,729 filed Mar. 12, 2021 (now U.S. Pat. No. 12,214,041), which in turn is the U.S. national phase of International Application No. PCT/US2019/051289 filed Sep. 16, 2019, and claims priority to European Patent application Ser. No. 18/197,763.8, filed Sep. 28, 2018 and U.S. Provisional Application No. 62/732,073, filed Sep. 17, 2018, the entire contents of each of which are hereby incorporated by reference.

FIELD

The disclosed inventions pertain to medical devices comprising polyurethanes, the polyurethanes themselves, compositions that may be useful for forming polyurethanes, medical devices, and methods for forming medical devices and polyurethanes.

BACKGROUND

Polymer excipients are commonly used in medical devices. Examples of typical polymer excipients are ethylene-vinyl acetate, silicone, or degradable polymers such as PLLA or PLGA. Polymer excipients are desirable because they allow for the diffusion-controlled, sustained release of a drug without regular patient intervention, thereby increasing compliance with treatment.

Polyurethane excipients are known. Polyurethane excipients may be biodegradable or biostable. Examples of biostable polyurethane excipients can be found in WO2012/066000 to Ward, et al. Biostable excipients are typically extracted from the body after the desired delivery period of the bioactive agent is completed.

SUMMARY

Known polyurethane excipients may require the use of catalysts that can cause cytotoxicity. Additionally, the polyurethane may be hydrophobic and not allow for the release of water soluble drugs, or certain drugs may be poorly soluble in the polyurethane. Furthermore, the use of aromatic hard segments may lead to the formation of harmful methylenedianiline.

In an embodiment, a polyurethane is provided having good biostability, a melting point of 140° C. or less, and a weight average molecular weight of from 100,000 to 500,000 g/mol. In an embodiment, the polyurethane is biostable. By biostable it is meant that the polyurethane remains chemically stable for at least 6 months in vivo. In an embodiment, the polyurethane is biostable for at least one year in vivo. In an embodiment, the polyurethane is biostable for from 6 months to 1 year after implantation. In an embodiment, the polyurethane offers improved solubility for water-soluble drugs over silicone-containing materials and EVA.

In an embodiment, a polyurethane comprises the residues of:
  i. an aliphatic diisocyanate,
  ii. an aliphatic diol comprising a poly(ethylene oxide) moiety,
  iii. an aliphatic diol comprising a polycarbonate moiety, and
  iv. a chain extender;

wherein the polyurethane has a melting temperature of 140° C. or less and has a weight average molecular weight of from 100,000 to 500,000 g/mol. In an embodiment, the polyurethane is substantially devoid of catalyst. In an embodiment, the polyurethane is devoid of catalyst. In an embodiment, the polyurethane is formed by reactive extrusion. In an embodiment, a medical device comprises the polyurethane and a bioactive agent.

The medical devices, methods, and polyurethanes may exhibit benefits in end-product biostability, drug release profile, health and safety, and processing speed or reproducibility.

DETAILED DESCRIPTION

In an embodiment, a medical device comprises a polyurethane and a bioactive agent. In an embodiment, the polyurethane is compounded with the bioactive agent and formed into a device by a melt-processing technique. The melt-processing technique may be (co) extrusion, injection molding, or 3D printing, such as by fused deposition modeling. In an embodiment, the polyurethane is compounded with the bioactive agent and extruded to form a medical device.

In an embodiment, the medical device is in the shape of a rod, tube or ring. In an embodiment, a method of forming a medical device comprises the step of forming at least a portion of a medical device from a melt comprising the polyurethane and a bioactive agent. In an embodiment, a method of forming a medical device comprises the step of extruding at least a portion of a medical device from a melt comprising the polyurethane and a bioactive agent.

The medical devices may have utility in the sustained release of drugs via an implantable device. The medical device may be implantable in the upper arm or intravaginally and have utility as a birth control or anti-viral device.

Polyurethane

In accordance with an embodiment, the polyurethane comprises the residues of:
  i. an aliphatic diisocyanate,
  ii. an aliphatic diol comprising a poly(ethylene oxide) moiety,
  iii. an aliphatic diol comprising a polycarbonate moiety, and
  iv. a chain extender;
  wherein the polyurethane has a melting temperature of 140° C. or less and has a weight average molecular weight of from 100,000 to 500,000 g/mol.

In an embodiment, the polyurethane is formed by polymerizing a composition comprising:
  i. a pre-polymer formed by polymerizing a pre-polymer composition comprising:
    1. an aliphatic diisocyanate,
    2. an aliphatic diol comprising a poly(ethylene oxide) moiety, and
    3. an aliphatic diol comprising a polycarbonate moiety,
  ii. a chain extender;
  In an embodiment, the polyurethane has a melting temperature of at least 50° C., at least 55° C., at least 60° C., or at least 63° C. In an embodiment, the polyurethane has a melting temperature of at most 135° C., at most 130° C., at most 125° C., at most 120° C., at most 115° C., at most 110° C., at most 105° C., at most 100° C., at most 95° C., at most 90° C., at most 85° C., at most 80° C., at most 75° C., at most 70° C., or at most 65° C.

In an embodiment, the polyurethane has a weight average molecular weight of at least 125,000 g/mol, at least 150,000 g/mol, at least 175,000 g/mol, at least 200,000 g/mol, at least 225,000 g/mol, at least 250,000 g/mol, at least 275,000 g/mol, at least 300,000 g/mol, at least 325,000 g/mol, or at least 350,000 g/mol. In an embodiment, the polyurethane has a weight average molecular weight of at most 475,000 g/mol, at most 450,000 g/mol, at most 425,000 g/mol, at most 400,000 g/mol, at most 375,000 g/mol, at most 350,000 g/mol, at most 325,000 g/mol, at most 300,000 g/mol, at most 275,000 g/mol, or at most 250,000 g/mol.

The polyurethane is typically formed by first forming a pre-polymer by polymerizing a pre-polymer composition comprising the aliphatic diisocyanate, the aliphatic diol comprising a poly(ethylene oxide) moiety, and the aliphatic diol comprising a polycarbonate moiety. The pre-polymer is then reacted with the chain extender to form a polyurethane having the desired molecular weight. In an embodiment, the polyurethane is linear. In an embodiment, the polyurethane is branched.

In an embodiment, the polyurethane or medical device is substantially devoid of catalyst. In an embodiment, the polyurethane or medical device is devoid of catalyst. Examples of catalysts are stannous octoate, dibutyltin dilaurate, and amine catalysts.

In an embodiment, the pre-polymer has a NCO/OH ratio of at least 0.95 and at most 1.01. In an embodiment, the pre-polymer has a NCO/OH ratio of at least 0.96, at least 0.97, at least 0.98, at least 0.99, or at least 0.995. In an embodiment, the pre-polymer has a NCO/OH ratio of at most 1.0.

In an embodiment, a processing aid is used. In an embodiment, the processing aid is a wax. Exemplary waxes are bis-stearamide waxes or polyethylene waxes. Thus, in an embodiment, a medical device comprises a processing aid.

In an embodiment, the polyurethane is formed by reactive extrusion by combining streams of pre-polymer and chain extender in an extruder. Following the reactive extrusion, it is expected that about 0.01-0.1 wt % of unreacted isocyanate will remain in the polyurethane.

In an embodiment, this unreacted isocyanate is then substantially reacted by post-curing the polyurethane at a temperature of at most 90° C. In an embodiment, post-curing is performed at a temperature of at least 50° C., at least 55° C., or at least 59° C. In an embodiment, post-curing is performed at a temperature of at most 85° C., at most 80° C., at most 75° C., at most 70° C., or at most 65° C.

In an embodiment, the post-curing is carried out until the microstructure of the polyurethane is completely formed, in other words, until the hard (isocyanate-containing) blocks and soft (polycarbonate or polyethylene oxide containing) blocks are sufficiently phase separated. In an embodiment, the duration of post-curing is at least 48 hours or at least 72 hours. In an embodiment, the duration of post-curing is from 48 to 96 hours. Whether the material has been sufficient post-cured will depend on both the duration and the temperature.

A typical reactive extruder allows for the modification of temperatures of various melt zones and plates. The ideal temperature settings will differ depending on the design of the reactive extruder and the characteristics of the polymer melt.

Melting points of the polyurethane are measured by DSC using the procedure detailed in the Examples. Two values related to melting temperature are obtained: the $T_m$ onset and the $T_m$ offset. The $T_m$ onset corresponds to the onset of melting of the crystalline domains of the polyurethane. The $T_m$ offset corresponds to the temperature at which substantially all of the crystalline domains of the polyurethane are melted, i.e. the polyurethane is fully molten.

Throughout this application, the melting temperature is defined as the $T_m$ offset, i.e. the temperature at which the polyurethane is fully molten. In case of multiple melting peaks, and therefore multiple $T_m$ onsets and $T_m$ offsets, the highest $T_m$ offset corresponds to the melting temperature of the polyurethane.

In an embodiment, the polyurethane, after post-curing, has a melting temperature of at least 95° C., at least 100° C., at least 105° C., at least 110° C., or at least 113° C. In an embodiment, the polyurethane, after post-curing, has a melting temperature of at most 135° C., at most 130° C., at most 125° C., at most 120° C., at most 115° C., or at most 110° C.

In an embodiment, the polyurethane, after post-curing, has a melting temperature onset ($T_m$ onset) of at least 50° C., at least 55° C., at least 60° C., at least 62° C., or at least 63° C. In an embodiment, the polyurethane, after post-curing, has a melting temperature onset ($T_m$ onset) of at most 110° C., at most 105° C., at most 100° C., at most 95° C., at most 90° C., at most 85° C., at most 80° C., at most 75° C., at most 70° C., or at most 65° C.

In an embodiment, the polyurethane, after post-curing, has a weight average molecular weight of at least 125,000 g/mol, at least 150,000 g/mol, at least 175,000 g/mol, at least 200,000 g/mol, at least 225,000 g/mol, at least 250,000 g/mol, at least 275,000 g/mol, at least 300,000 g/mol, at least 325,000 g/mol, or at least 350,000 g/mol. In an embodiment, the polyurethane, after post-curing, has a weight average molecular weight of at most 475,000 g/mol, at most 450,000 g/mol, at most 425,000 g/mol, at most 400,000 g/mol, at most 375,000 g/mol, at most 350,000 g/mol, at most 325,000 g/mol, at most 300,000 g/mol, at most 275,000 g/mol, or at most 250,000 g/mol.

In an embodiment, the polyurethane comprises the residues of the following components.

Aliphatic Diisocyanate Component

The polyurethane comprises the residue of an aliphatic diisocyanate. In an embodiment, the aliphatic diisocyanate comprises an average of at least 1.9 isocyanate groups per molecule and an average of less than 2.7 isocyanate groups per molecule.

In an embodiment, the aliphatic diisocyanate comprises hexamethylene diisocyanate (HDI), tetramethylene-1,4-diisocyanate, cyclohexane-1,4-diisocyanate, dicyclohexyl-methane-4,4'-diisocyanate (HMDI), isophorone diisocyanate (IPDI), or a mixture thereof. In an embodiment, the aliphatic diisocyanate consists of hexamethylene diisocyanate (HDI), tetramethylene-1,4-diisocyanate, cyclohexane-1,4-diisocyanate, dicyclohexylmethane-4,4'-diisocyanate (HMDI), isophorone diisocyanate (IPDI), or a mixture thereof. In an embodiment, the aliphatic diisocyanate consists of dicyclohexylmethane-4,4'-diisocyanate.

In an embodiment, the molecular weight of the diisocyanate is from 100 to 500 g/mol. In an embodiment, the molecular weight of the diisocyanate is from 150 to 260 g/mol.

In an embodiment, the polyurethane comprises at least 10 wt %, at least 20 wt %, at least 25 wt %, or at least 30 wt % of the residue of an aliphatic diisocyanate, based on the total weight of the polyurethane. In an embodiment, the polyurethane comprises at most 50 wt %, at most 45 wt %, at most 40 wt %, or at most 35 wt % of the residue of an aliphatic diisocyanate, based on the total weight of the polyurethane. In an embodiment, the pre-polymer composition comprises at least 10 wt %, at least 20 wt %, at least 25 wt %, or at least 30 wt % of aliphatic diisocyanate, based on the total weight of the composition. In an embodiment, the pre-polymer composition comprises at most 50 wt %, at most 45 wt %, at most 40 wt %, or at most 35 wt % aliphatic diisocyanate, based on the total weight of the composition.

Aliphatic Diol Comprising a Poly(Ethylene Oxide) Moiety

The polyurethane comprises the residue of an aliphatic diol comprising a poly(ethylene oxide) moiety. Typically, the diol comprises two OH groups and a poly(ethylene oxide) backbone. The OH groups may be directly attached to the backbone, or may be separated by a linker. For example, a hydroxyalkyl terminated poly(ethylene oxide) is an aliphatic diol comprising a poly(ethylene oxide) moiety.

In an embodiment, the aliphatic diol comprising a poly(ethylene oxide) moiety has a weight average molecular weight of from 500 to 2000 g/mol. In an embodiment, the aliphatic diol comprising a poly(ethylene oxide) moiety has a weight average molecular weight of at least 600 g/mol, at least 650 g/mol, at least 750 g/mol, at least 800 g/mol, at least 900 g/mol, or at least 950 g/mol. In an embodiment, the aliphatic diol comprising a poly(ethylene oxide) moiety has a weight average molecular weight of at most 1900 g/mol, at most 1800 g/mol, at most 1700 g/mol, at most 1600 g/mol, at most 1500 g/mol, at most 1400 g/mol, at most 1300 g/mol, or at most 1200 g/mol.

In an embodiment, the polyurethane comprises at least 2 wt %, at least 3 wt %, at least 4 wt %, at least 5 wt %, or at least 6 wt % of the residue of an aliphatic diol comprising a poly(ethylene oxide) moiety, based on the total weight of the polyurethane. In an embodiment, the polyurethane comprises at most 15 wt %, at most 12 wt %, at most 10 wt %, or at most 9 wt % of the residue of aliphatic diol comprising a poly(ethylene oxide) moiety, based on the total weight of the polyurethane. In an embodiment, the aliphatic diol comprising a poly(ethylene oxide) moiety is present in an amount of at least 2 wt %, at least 3 wt %, at least 4 wt %, at least 5 wt %, or at least 6 wt %, based on the total weight of the composition. In an embodiment, the aliphatic diol comprising a poly(ethylene oxide) moiety is present in an amount of at most 15 wt %, at most 12 wt %, at most 10 wt %, or at most 9 wt %, based on the total weight of the composition.

Aliphatic Diol Comprising a Polycarbonate Moiety

The polyurethane comprises the residue of an aliphatic diol comprising a polycarbonate moiety. Typically, the diol comprises two OH groups and a polycarbonate backbone. The OH groups may be directly attached to the backbone or may be separated by a linker. For example, a hydroxyalkyl terminated polycarbonate is an aliphatic diol comprising a polycarbonate moiety.

In an embodiment, the aliphatic diol comprising a polycarbonate moiety has a weight average molecular weight of from 500 to 2000 g/mol. In an embodiment, the aliphatic diol comprising a polycarbonate moiety has a weight average molecular weight of at least 600 g/mol, at least 650 g/mol, at least 750 g/mol, at least 800 g/mol, at least 900 g/mol, or at least 950 g/mol. In an embodiment, the aliphatic diol comprising a polycarbonate moiety has a weight average molecular weight of at most 1900 g/mol, at most 1800 g/mol, at most 1700 g/mol, at most 1600 g/mol, at most 1500 g/mol, at most 1400 g/mol, at most 1300 g/mol, or at most 1200 g/mol.

In an embodiment, the aliphatic diol comprising a polycarbonate moiety has a weight average molecular weight that is no more than 250 g/mol, no more than 200 g/mol, no more than 150 g/mol, no more than 100 g/mol, or no more than 50 g/mol different than the weight average molecular weight of the aliphatic diol comprising a poly(ethylene oxide) moiety.

In an embodiment, the polyurethane comprises at least 30 wt %, at least 35 wt %, at least 40 wt %, at least 45 wt %, or at least 50 wt % of the residue of an aliphatic diol comprising a polycarbonate moiety, based on the total weight of the polyurethane. In an embodiment, the polyurethane comprises at most 70 wt %, at most 65 wt %, at most 60 wt %, or at most 55 wt % of the residue of aliphatic diol comprising a polycarbonate moiety, based on the total weight of the polyurethane. In an embodiment, the aliphatic diol comprising a polycarbonate moiety is present in an amount of at least 30 wt %, at least 35 wt %, at least 40 wt %, at least 45 wt %, or at least 50 wt %, based on the total weight of the composition. In an embodiment, the aliphatic diol comprising a polycarbonate moiety is present in an amount of at most 70 wt %, at most 65 wt %, at most 60 wt %, or at most 55 wt %, based on the total weight of the composition.

Chain Extender

The polyurethane comprises the residue of a chain extender. A chain extender is an alkane diol having from 2 to 20 carbon atoms, wherein one or more carbon atoms may be substituted with oxygen. In an embodiment, the chain extender has a molecular weight of at least 60 g/mol, at least 70 g/mol, at least 80 g/mol, at least 90 g/mol, or at least 100 g/mol. In an embodiment, the chain extender has a molecular weight of at most 500 g/mol, at most from 400 g/mol, at most 300 g/mol, at most 200 g/mol, or at most 150 g/mol.

In an embodiment, the chain extender comprises ethylene glycol, diethylene glycol, propylene glycol, dipropylene glycol, 1,3-propanediol, 1,4-butanediol, 1,5-pentanediol, 1,6-hexanediol, or 1,8-octanediol. In an embodiment, the chain extender consists of ethylene glycol, diethylene glycol, propylene glycol, dipropylene glycol, 1,3-propanediol, 1,4-butanediol, 1,5-pentanediol, 1,6-hexanediol, or 1,8-octanediol, or a mixture thereof. In an embodiment, the chain extender consists of 1,4-butanediol, 1,6-hexanediol, or a mixture thereof.

In an embodiment, the polyurethane comprises at least 1 wt %, at least 2 wt %, at least 3 wt %, at least 4 wt %, or at least 5 wt % of the residue of a chain extender, based on the total weight of the polyurethane. In an embodiment, the polyurethane comprises at most 12 wt %, at most 10 wt %, at most 9 wt %, at most 8 wt %, at most 7 wt %, or at most 6 wt %, of the residue of a chain extender, based on the total weight of the polyurethane. In an embodiment, the composition comprises at least 1 wt %, at least 2 wt %, at least 3 wt %, at least 4 wt %, or at least 5 wt % of the chain extender, based on the total weight of the composition. In an embodiment, the composition comprises at most 12 wt %, at most 10 wt %, at most 9 wt %, at most 8 wt %, at most 7 wt %, or at most 6 wt %, of a chain extender, based on the total weight of the composition.

Other Optional Features of the Polyurethane

In an embodiment, the polyurethane is devoid of silicone. In an embodiment, the polyurethane is substantially devoid of silicone. In an embodiment, the composition is devoid of silicone-containing moieties. In an embodiment, the composition is substantially devoid of silicone-containing moieties. In an embodiment, the composition comprises less than 0.1 wt % of silicone silicone-containing moieties, based on the total weight of the composition.

In an embodiment, the polyurethane is devoid of endgroups. An endgroup is a moiety that is separately present at a terminal end of a molecule. An endgroup may be unique from moieties in the backbone. An endgroup may be formed by reacting a terminal isocyanate group present after forming the polymer backbone with a coreactive group on a monofunctional moiety. For instance, a terminal isocyanate group may be reacted with 1-octanol or octylamine to form a C8 alkyl endgroup. Endgroups may also result from the inclusion of chain stoppers, such as monofunctional alcohols, in a formulation used in the formation of a polyurethane. For instance, a formulation for forming a polyurethane may comprise a diisocyanate, a polymeric aliphatic diol, a chain extender, and a monofunctional alcohol.

In an embodiment, the polyurethane is devoid of endgroups. In an embodiment, the polyurethane is substantially devoid of endgroups. In an embodiment, the polyurethane comprises less than 0.1 wt % of endgroups, based on the total weight of the polyurethane.

Bioactive Agents

In an embodiment, a medical device comprises the polyurethane and a bioactive agent. In an embodiment, the bioactive agent is dispersed in the polyurethane. In an embodiment, the bioactive agent is solubilized in the polyurethane. In an embodiment, the amount of bioactive agent in the polyurethane exceeds the solubility limit of the drug in the polyurethane.

Examples of bioactive agents are anesthetic agents, analgesic agents, antibacterial agents, antifungal agents, antiviral agents, contraceptive agents, hormones or prohormones, or combinations thereof.

In an embodiment, the bioactive agent has a melting temperature that is higher than the melting temperature of the polyurethane. In an embodiment, the bioactive agent has a melting temperature of from 150° C. to 200° C.

The Examples below further elucidate embodiments of the invention, but of course, should not be construed as in any way limiting the scope of the claims.

EXAMPLES

Measurement Methods

Molecular Weight. Weight average molecular weight is measured via gel permeation chromatography (GPC) according to ISO 13885-1:2008.

NCO/OH. NCO value is measured according to ASTM D 2572-97. Hydroxyl values are respectively determined titrimetrically according to ISO 4629-1978.

Melting point(s). The melting point(s) are measured by differential scanning calorimetry (DSC). Measurements are performed using a TA Instruments Discovery Q200. Pellets are weighed and sealed in an aluminum pan. The sample is cooled from room temperature to −90° C. at a ramp rate of 10° C./min. The sample is then heated to 250° C. at 10° C./min followed again by cooling to −90° C. at 10° C./min. The sample is then heated again (second heating run) to 250° C. at 10° C./min. The Tg, $T_m$ onset, and $T_m$ offset of the material are determined during this second heating run. The $T_m$ onset is the point at which the heat flow vs. temperature curve changes inflection due to the onset of melting. The $T_m$ offset is the point at which the heat flow vs. temperature curve returns to its normal trajectory after the polyurethane is fully molten.

Hardness. A PTC Instruments Model #307L, ASTM Type A durometer is used. Film samples are placed on the Shore A Hardness stage opposite a 1 kg counter weight. The measurement is completed at least 5 times in different locations and the average taken. Two separate samples are tested and the results averaged.

Tensile modulus, tensile elongation at break, and tensile strength are measured according to ASTM D638.

Melt flow index. Melt flow is the determination of polymer flow characteristics in terms of polymer extrudate (g) per 10 minutes. Melt flow index is measured according to a modified version of ASTM 1238. This test is completed utilizing different loads of weight depending on the polymer being tested. The polymer is loaded into the barrel of a melt indexer instrument and allowed to completely melt. An operator then manually cuts the material at certain time increments. Each sample cut is then weighed. A minimum of two cuts is made in the material; preferably, three cuts are made. The mass of each sample cut is then multiplied to determine the mass of sample over a 10-minute period. These values are averaged and reported as the melt flow index.

Example 1

Pre-Polymer Synthesis

The composition of the pre-polymer is shown in Table 1-1. The wt % is based on the total weight of the prepolymer. The polycarbonate polyol is CD210 from Daicel. Prior to synthesis, polycarbonate diol and polyethylene glycol are heated and sparged with nitrogen to remove residual water. The materials are tested via Karl Fischer titration to ensure water content is ≤150 ppm prior to starting prepolymer synthesis.

Under the flow of nitrogen, HMDI is charged into a 40-gallon Myers Mixer reactor and heated to 75° C. Polycarbonate diol is then charged into the reactor at a rate of 1.0 kg/min. Polyethylene glycol is then charged into the reactor at a rate of 1.0 kg/min. Once polyethylene glycol addition is complete, the reactor is heated to 82° C. and the prepolymer components mix for 30 minutes. The prepolymer is degassed using vacuum and dispensed into a pressure pot.

TABLE 1-1

| | | | | | |
|---|---|---|---|---|---|
| Pre-polymer Composition | | | | | |
| Material | MW of Reactant | Moles | MW Contribution | Wt. % | |
| HMDI | 262.35 | 3.7338 | 979.55 | 35.30 | |
| Polycarbonate diol | 984.39 | 1.6 | 1575.02 | 56.75 | |
| Polyethylene glycol | 991 | 0.2229 | 220.89 | 7.96 | |

The theoretical molecular weight of the pre-polymer is 1524 g/mol.

Reactive Extrusion of Polyurethane

Streams of pre-polymer and chain extender (butanediol, MW=90.12 g/mol) are combined in a Leistritz Extrusion Corp. Micro 27 extruder. The ratio of pre-polymer to chain extender is modified to obtain polyurethanes with different NCO/OH ratio. The approximate final composition of the polyurethane at 1.01 NCO/OH is shown in Table 1-2.

TABLE 1-2

| | | | | | |
|---|---|---|---|---|---|
| Final Polyurethane Composition | | | | | |
| Material | Mw of Reactant (g/mol) | Moles | Mw Contribution (g/mol) | Wt. % | |
| HMDI | 262.35 | 3.7338 | 979.55 | 33.27 | |
| Polycarbonate diol | 984.39 | 1.6 | 1575.02 | 53.49 | |

TABLE 1-2-continued

| | Final Polyurethane Composition | | | |
|---|---|---|---|---|
| Material | Mw of Reactant (g/mol) | Moles | Mw Contribution (g/mol) | Wt. % |
| Polyethylene glycol | 991 | 0.2229 | 220.89 | 7.5 |
| Butanediol | 90.12 | 1.8739 | 168.88 | 5.74 |

After leaving the extruder, it is expected that the polyurethane has from 0.01-0.1 wt % unreacted isocyanate. This unreacted isocyanate is then substantially reacted by post-curing at the stated cure temperature.

The melting points of the resulting polyurethanes are shown in Table 1-3.

TABLE 1-3

| | Melting Points of polyurethanes formed by reactive extrusion. | | | | | |
|---|---|---|---|---|---|---|
| Sample | Melting points (° C.), 60° C. cure, 72 hrs | | Melting points (° C.), 80° C. cure, 48 hrs | | Melting points (° C.), 100° C. cure | |
| (NCO/OH) | Tm Onset | Tm Offset | Tm Onset | Tm Offset | Tm Onset | Tm Offset |
| 0.98 | 64.6 | 113.3 | 69.1 | 129.0 | >160 | >160 |
| 0.99 | 62.9 | 118.1 | 68.7 | 126.1 | >160 | >160 |
| 1.00 | 66.0 | 117.8 | 72.5 | 128.1 | >160 | >160 |

It is found that the produced polyurethanes are able to be post-cured at low temperatures and result in a significantly lower melting temperature than other polyurethanes, which typically have a melting point of over 180° C. 5 Other properties of the polyurethanes are shown in Table 1-4. nm=not measured

TABLE 1-4

| | 0.98 NCO/OH | Std. Dev. | 0.99 NCO/OH | Std. Dev. | 1.00 NCO/OH | Std. Dev. |
|---|---|---|---|---|---|---|
| | Further measured properties of polyurethanes formed by reactive extrusion | | | | | |
| Hardness (60° C. post-cure) (Shore A) | 75 | 1.605 | 78.5 | 1.34 | 75.5 | 0.845 |
| MFI (180° C.) 80° C. post-cure) (g/10 min) | 13.65 | 1.08 | 4.33 | 0.42 | 2.6 | 0.2 |
| Tensile Modulus (80° C. post-cure) (MPa) | 3.327 | 17.67 | 3.495 | 17.36 | 3.414 | 13.31 |
| Tensile Elongation at Break (80° C. post-cure) (%) | 548.10 | 13.50 | 535.30 | 14.20 | 564.93 | 43.25 |
| Tensile Strength (80° C. post-cure) (MPa) | 30.00 | 143.2 | 24.38 | 122.00 | 26.63 | 1943.6 |
| Molecular Weight (60° C. post-cure) (Mw) (g/mol) | 168660 | 4906 | 222336 | 6357 | nm | nm |
| Molecular Weight (80° C. post-cure) (Mw) (g/mol) | nm | nm | 224041 | 3025.71 | 371484 | 22880 |
| DSC Tg (80° C. post-cure) 1st Heating Run (° C.) | −7.16 | 2.505 | −7.97 | 1.078 | −6.083 | 1.09 |
| DSC Tg (80° C. post-cure) 2nd Heating Run (°C) | −6.79 | 0.618 | −7.96 | 1.093 | −5.32 | 4.33 |
| DSC Tg (60° C. post-cure) 1st Heating Run (° C.) | −11.64 | 0.559 | −9.63 | 0.446 | −8.172 | 2.137 |
| DSC Tg (60° C. post-cure) 2nd Heating Run (° C.) | −1.55 | 4.809 | −2.69 | 4.125 | −7.76 | 2.44 |

Example 2

Formation of Polyurethanes

Moisture is removed from the polycarbonate diol (CD210, MW 967.24 g/mol), polyethylene glycol (PEG-1000, MW 1003 g/mol), and chain extender, butanediol (MW 90.12 g/mol), by sparging with nitrogen. The polycarbonate diol is charged to an open, dried, 400 mL kettle reactor. The reactor is then assembled and heated to an internal temperature of 70° C. Once the setpoint is reached, the isocyanate (dicyclohexylmethane-4,4'-diisocyanate (HMDI) or hexamethylene diisocyanate (HDI)) is slowly charged to reactor. The exotherm is noted, then the mantle is set to 85° C. and mixed for two hours. The polyethylene glycol is then charged to reactor, the exotherm noted, and the prepolymer mixed for two hours.

Using a high-speed mixer (Silverson LR5), the butanediol is blended into each prepolymer at 5000 rpm for 3 minutes. The samples are cast into molds and placed in an oven.

The polyurethanes formed are shown in Table 2-1. Amounts are in wt % based on the total weight of the polyurethane.

TABLE 2-1

| | Example 2 Polyurethanes | | | | | |
|---|---|---|---|---|---|---|
| Sample | Poly-carbonate Diol (wt %) | Poly-ethylene Oxide (wt %) | HMDI (wt %) | HDI (wt %) | Butanediol (wt %) | MW (g/mol) |
| 2A | 52.79 | 8.21 | 33.32 | | 5.68 | 112,700 |
| 2B | 51.00 | 10.00 | 33.32 | | 5.68 | 163,717 |
| 2C | 49.00 | 12.00 | 33.31 | | 5.69 | 124,916 |
| 2D | 52.79 | 8.21 | | 29.23 | 9.76 | 87,985 |

Hardness and melting temperatures were measured after curing at 80° C. for 48 hours and then allowing the samples to cool in a fume hood for 24 hours. The results are presented in Table 2-2.

TABLE 2-2

| | Results after curing at 80° C. for 48 hours | | |
|---|---|---|---|
| Sample | Hardness (Shore A) | Tm Onset (° C.) | Tm Offset (° C.) |
| 2A | 80.5 | 46.1 | 126.9 |
| 2B | 80.2 | 47.2 | 119.1 |
| 2C | 80.6 | 50.5 | 123.8 |
| 2D | 89.2 | nm | nm |

Melting temperatures were measured after curing at curing at 60° C. for 72 hours instead of 80° C. at 48 hours as above. The hardness is expected to be the same and the $T_m$ Offset is substantially the same for samples 2A and 2C. $T_m$ Onset increases substantially. It is believed that bulk properties of the polymer, such as hardness and $T_m$ Offset, are sufficiently defined after 48 hours at 80° C., but that the microstructure was not entirely formed at that time. Results after 60° C. for 72 hours are shown in Table 2-3.

TABLE 2-3

| | Results after curing at 60° C. for 72 hours | |
|---|---|---|
| Sample | Tm Onset (° C.) | Tm Offset (° C.) |
| 2A | 71.2 | 124.7 |
| 2B | 72.6 | 97.3 |
| 2C | 71.9 | 125.8 |
| 2D | nm | nm |

Additional Description of Exemplary Embodiments

1. A medical device comprising:
   a. a polyurethane comprising the residues of:
      i. an aliphatic diisocyanate,
      ii. an aliphatic diol comprising a poly(ethylene oxide) moiety,
      iii. an aliphatic diol comprising a polycarbonate moiety, and
      iv. a chain extender; and
   b. a bioactive agent,
   wherein the polyurethane has a melting temperature of 140° C. or less and has a weight average molecular weight of from 100,000 to 500,000 g/mol.
2. A polyurethane comprising the residues of:
   i. an aliphatic diisocyanate,
   ii. an aliphatic diol comprising a poly(ethylene oxide) moiety,
   iii. an aliphatic diol comprising a polycarbonate moiety, and
   iv. a chain extender;

wherein the polyurethane has a melting temperature of 140° C. or less and has a weight average molecular weight of from 100,000 to 500,000 g/mol.
3. The medical device or polyurethane of any one of the previous exemplary embodiments, wherein the polyurethane is formed by polymerizing a composition comprising:
   i. a pre-polymer formed by polymerizing a pre-polymer composition comprising:
      1. an aliphatic diisocyanate,
      2. an aliphatic diol comprising a poly(ethylene oxide) moiety, and
      3. an aliphatic diol comprising a polycarbonate moiety, and
   ii. a chain extender.
4. The medical device or polyurethane of any one of the previous exemplary embodiments, wherein the polyurethane is formed by polymerizing a composition that is devoid of or substantially devoid of catalyst.
5. The medical device or polyurethane according to any one of the previous exemplary embodiments, wherein the polyurethane is formed by reactive extrusion.
6. The medical device or polyurethane according to any one of the previous exemplary embodiments, wherein the polyurethane has a melting temperature of at least 95° C., at least 100° C., at least 105° C., at least 110° C., or at least 113° C.
7. The medical device or polyurethane according to any one of the previous exemplary embodiments, wherein the polyurethane has a melting temperature of at most 135° C., at most 130° C., at most 125° C., at most 120° C., at most 115° C., or at most 110° C.
8. The medical device or polyurethane according to any one of the preceding exemplary embodiments, wherein the polyurethane, after post-curing, has a melting temperature onset ($T_m$ onset) of at least 50° C., at least 55° C., at least 60° C., at least 62° C., or at least 63° C.
9. The medical device or polyurethane according to any one of the preceding exemplary embodiments, wherein the polyurethane, after post-curing, has a melting temperature onset ($T_m$ onset) of at most 110° C., at most 105° C., at most 100° C., at most 95° C., at most 90° C., at most 85° C., at most 80° C., at most 75° C., at most 70° C., or at most 65° C.
10. The medical device or polyurethane method according to any one of the preceding exemplary embodiments, wherein the polyurethane has a weight average molecular weight of at least 125,000 g/mol, at least 150,000 g/mol, at least 175,000 g/mol, at least 200,000 g/mol, at least 225,000 g/mol, at least 250,000 g/mol, at least 275,000 g/mol, at least 300,000 g/mol, at least 325,000 g/mol, or at least 350,000 g/mol.
11. The medical device or polyurethane according to any one of the preceding exemplary embodiments, wherein the polyurethane has a weight average molecular weight of at most 475,000 g/mol, at most 450,000 g/mol, at most 425,000 g/mol, at most 400,000 g/mol, at most 375,000 g/mol, at most 350,000 g/mol, at most 325,000 g/mol, at most 300,000 g/mol, at most 275,000 g/mol, or at most 250,000 g/mol.
12. A method of forming a polyurethane suitable for use in a medical device, comprising the steps of:
   a. reactively extruding a composition comprising:
      i. a pre-polymer formed from a pre-polymer composition comprising:
         1. an aliphatic diisocyanate,
         2. an aliphatic diol comprising a poly(ethylene oxide) moiety, and 3. an aliphatic diol comprising a polycarbonate moiety, and
   ii. a chain extender;
thereby forming a polyurethane, wherein the composition is substantially devoid of catalyst,
   b. post-curing the polyurethane at a temperature of at most 90° C., and wherein, after post-curing, the polyurethane has a melting temperature of 140° C. or less and has a weight average molecular weight of from 100,000 to 500,000 g/mol.

13. The method according to any one of the previous exemplary embodiments, wherein post-curing is performed at a temperature of at least 50° C., at least 55° C., or at least 59° C.

14. The method according to any one of the previous exemplary embodiments, wherein post-curing is performed at a temperature of at most 85° C., at most 80° C., at most 75° C., at most 70° C., or at most 65° C.

15. The method according to any one of the previous exemplary embodiments, wherein the polyurethane, after post-curing, has a melting temperature of at least 95° C., at least 100° C., at least 105° C., at least 110° C., or at least 113° C.

16. The method according to any one of the previous exemplary embodiments, wherein the polyurethane, after post-curing, has a melting temperature of at most 135° C., at most 130° C., at most 125° C., at most 120° C., at most 115° C., or at most 110° C.

17. The method according to any one of the previous exemplary embodiments, wherein post-curing occurs until the microstructure of the polyurethane is completely formed.

18. The method according to any one of the previous exemplary embodiments, wherein the duration of post-curing is at least 48 hours.

19. The method according to any one of the previous exemplary embodiments, wherein the duration of post-curing is at least 72 hours.

20. The method according to any one of the previous exemplary embodiments, wherein the duration of post-curing is at from 48 to 96 hours.

21. The method according to any one of the previous exemplary embodiments, wherein the duration of post-curing is at from 72 to 96 hours.

22. A polyurethane formed by the method of any one of the preceding exemplary embodiments.

23. A method of forming a medical device comprising the step of forming at least a portion of a medical device from a melt comprising the polyurethane according to any one of the previous claims and a bioactive agent.

24. The method according to the previous exemplary embodiment, wherein the method comprises melt processing the melt, preferably by (co) extrusion, injection molding, or 3D printing.

25. A medical device formed by the method of any one of the preceding exemplary embodiments.

26. The medical device, polyurethane, or method according to any one of the preceding exemplary embodiments, wherein the polyurethane, after post-curing, has a weight average molecular weight of at least 125,000 g/mol, at least 150,000 g/mol, at least 175,000 g/mol, at least 200,000 g/mol, at least 225,000 g/mol, at least 250,000 g/mol, at least 275,000 g/mol, at least 300,000 g/mol, at least 325,000 g/mol, or at least 350,000 g/mol.

27. The medical device, polyurethane, or method according to any one of the preceding exemplary embodiments, wherein the polyurethane, after post-curing, has a weight average molecular weight of at most 475,000 g/mol, at most 450,000 g/mol, at most 425,000 g/mol, at most 400,000 g/mol, at most 375,000 g/mol, at most 350,000 g/mol, at most 325,000 g/mol, at most 300,000 g/mol, at most 275,000 g/mol, or at most 250,000 g/mol.

28. The medical device, polyurethane, or method according to any one of the previous exemplary embodiments, wherein the polyurethane has a melting temperature of at least 95° C., at least 100° C., at least 105° C., at least 110° C., or at least 113° C.

29. The medical device, polyurethane, or method according to any one of the previous exemplary embodiments, wherein the polyurethane has a melting temperature of at most 135° C., at most 130° C., at most 125° C., at most 120° C., at most 115° C., or at most 110° C.

30. The medical device, polyurethane, or method according to any one of the preceding exemplary embodiments, wherein the polyurethane, after post-curing, has a melting temperature onset ($T_m$ onset) of at least 50° C., at least 55° C., at least 60° C., at least 62° C., or at least 63° C.

31. The medical device, polyurethane, or method according to any one of the preceding exemplary embodiments, wherein the polyurethane, after post-curing, has a melting temperature onset ($T_m$ onset) of at most 110° C., at most 105° C., at most 100° C., at most 95° C., at most 90° C., at most 85° C., at most 80° C., at most 75° C., at most 70° C., or at most 65° C.

32. The medical device, polyurethane, or method according to any one of the preceding exemplary embodiments, wherein the polyurethane is biostable.

33. The medical device, polyurethane, or method according to any one of the preceding exemplary embodiments, wherein the polyurethane is biostable for at least one year in vivo.

34. The medical device, polyurethane, or method according to any one of the preceding exemplary embodiments, wherein the polyurethane is biostable from 6 to 12 months in vivo.

35. The medical device, polyurethane, or method according to any one of the preceding exemplary embodiments, wherein the polyurethane is substantially devoid of catalyst.

36. The medical device, polyurethane, or method according to any one of the preceding exemplary embodiments, wherein the polyurethane is devoid of catalyst.

37. The medical device, polyurethane, or method according to any one of the preceding exemplary embodiments, wherein the pre-polymer has a NCO/OH ratio of at least 0.95 and at most 1.01.

38. The medical device, polyurethane, or method according to any one of the preceding exemplary embodiments, wherein the pre-polymer has a NCO/OH ratio of at least 0.96, at least 0.97, at least 0.98, at least 0.99, or at least 0.995.

39. The medical device, polyurethane, or method according to any one of the preceding exemplary embodiments, wherein the pre-polymer has a NCO/OH ratio of at most 1.0.

40. The medical device, polyurethane, or method according to any one of the previous exemplary embodiments, wherein the polyurethane consists of the residues of:
   i. an aliphatic diisocyanate,
   ii. an aliphatic diol comprising a poly(ethylene oxide) moiety, iii. an aliphatic diol comprising a polycarbonate moiety, and iv. a chain extender.

41. The medical device, polyurethane, or method according to any one of the previous exemplary embodiments, wherein the composition consists of:

i. A pre-polymer formed from a composition consisting of:

1. an aliphatic diisocyanate, 2. an aliphatic diol comprising a poly(ethylene oxide) moiety, and 3. an aliphatic diol comprising a polycarbonate moiety, and ii. a chain extender.

42. The medical device, polyurethane, or method according to any one of the preceding exemplary embodiments, wherein the polymer is substantially devoid of diols comprising moieties other than a poly(ethylene oxide) moiety or a polycarbonate moiety.

43. The medical device, polyurethane, or method according to any one of the previous exemplary embodiments, wherein the aliphatic diisocyanate comprises hexamethylene diisocyanate (HDI), tetramethylene-1,4-diisocyanate, cyclohexane-1,4-diisocyanate, dicyclohexylmethane-4,4'-diisocyanate (HMDI), isophorone diisocyanate (IPDI), or a mixture thereof.

44. The medical device, polyurethane, or method according to any one of the previous exemplary embodiments, wherein the aliphatic diisocyanate consists of hexamethylene diisocyanate (HDI), tetramethylene-1,4-diisocyanate, cyclohexane-1,4-diisocyanate, dicyclohexylmethane-4,4'-diisocyanate (HMDI), isophorone diisocyanate (IPDI), or a mixture thereof.

45. The medical device, polyurethane, or method according to any one of the previous exemplary embodiments, wherein the aliphatic diisocyanate comprises hexamethylene diisocyanate, dicyclohexylmethane 4,4'-diisocyanate, isophorone diisocyanate, or a mixture thereof.

46. The medical device, polyurethane, or method according to any one of the previous exemplary embodiments, wherein the aliphatic diisocyanate consists of hexamethylene diisocyanate, dicyclohexylmethane 4,4'-diisocyanate, isophorone diisocyanate, or a mixture thereof.

47. The medical device, polyurethane, or method according to any one of the previous exemplary embodiments, wherein the aliphatic diisocyanate consists of dicyclohexylmethane-4,4'-diisocyanate.

48. The medical device, polyurethane, or method according to any one of the preceding exemplary embodiments, wherein the aliphatic diisocyanate comprises an average of from 1.9 to 2.7 isocyanate groups per molecule.

49. The medical device, polyurethane, or method according to any one of the preceding exemplary embodiments, wherein the aliphatic diisocyanate has a molecular weight of from 100 to 500 g/mol, or from 150 to 260 g/mol.

50. The medical device, polyurethane, or method according to any one of the preceding exemplary embodiments, wherein the polyurethane comprises at least 10 wt %, at least 20 wt %, at least 25 wt %, or at least 30 wt % of the residue of an aliphatic diisocyanate, based on the total weight of the polyurethane.

51. The medical device, polyurethane, or method according to any one of the preceding exemplary embodiments, wherein the polyurethane comprises at most 50 wt %, at most 45 wt %, at most 40 wt %, or at most 35 wt % of the residue of an aliphatic diisocyanate, based on the total weight of the polyurethane.

52. The medical device, polyurethane, or method according to any one of the preceding exemplary embodiments, wherein the pre-polymer composition comprises at least 10 wt %, at least 20 wt %, at least 25 wt %, or at least 30 wt % of aliphatic diisocyanate, based on the total weight of the composition.

53. The medical device, polyurethane, or method according to any one of the preceding exemplary embodiments, wherein the pre-polymer composition comprises at most 50 wt %, at most 45 wt %, at most 40 wt %, or at most 35 wt % aliphatic diisocyanate, based on the total weight of the composition.

54. The medical device, polyurethane, or method according to any one of the previous exemplary embodiments, wherein the aliphatic diol comprising a poly(ethylene oxide) moiety has a weight average molecular weight of from 500 to 2000 g/mol.

55. The medical device, polyurethane, or method according to any one of the previous exemplary embodiments, wherein the aliphatic diol comprising a poly(ethylene oxide) moiety has a weight average molecular weight of at least 600 g/mol, at least 650 g/mol, at least 750 g/mol, at least 800 g/mol, at least 900 g/mol, or at least 950 g/mol.

56. The medical device, polyurethane, or method according to any one of the previous exemplary embodiments, wherein the aliphatic diol comprising a poly(ethylene oxide) moiety has a weight average molecular weight of at most 1900 g/mol, at most 1800 g/mol, at most 1700 g/mol, at most 1600 g/mol, at most 1500 g/mol, at most 1400 g/mol, at most 1300 g/mol, or at most 1200 g/mol.

57. The medical device, polyurethane, or method according to any one of the preceding exemplary embodiments, wherein the polyurethane comprises at least 2 wt %, at least 3 wt %, at least 4 wt %, at least 5 wt %, or at least 6 wt % of the residue of an aliphatic diol comprising a poly(ethylene oxide) moiety, based on the total weight of the polyurethane.

58. The medical device, polyurethane, or method according to any one of the preceding exemplary embodiments, wherein the polyurethane comprises at most 15 wt %, at most 12 wt %, at most 10 wt %, or at most 9 wt % of the residue of aliphatic diol comprising a poly(ethylene oxide) moiety, based on the total weight of the polyurethane.

59. The medical device, polyurethane, or method according to any one of the previous exemplary embodiments, wherein the aliphatic diol comprising a poly(ethylene oxide) moiety is present in an amount of at least 2 wt %, at least 3 wt %, at least 4 wt %, at least 5 wt %, or at least 6 wt %, based on the total weight of the composition.

60. The medical device, polyurethane, or method according to any one of the previous exemplary embodiments, wherein the aliphatic diol comprising a poly(ethylene oxide) moiety is present in an amount of at most 15 wt %, at most 12 wt %, at most 10 wt %, or at most 9 wt %, based on the total weight of the composition.

61. The medical device, polyurethane, or method according to any one of the previous exemplary embodiments, wherein the aliphatic diol comprising a polycarbonate moiety has a weight average molecular weight of from 500 to 2000 g/mol.

62. The medical device, polyurethane, or method according to any one of the previous exemplary embodiments, wherein the aliphatic diol comprising a polycarbonate moiety has a weight average molecular weight of at least 600 g/mol, at least 650 g/mol, at least 750 g/mol, at least 800 g/mol, at least 900 g/mol, or at least 950 g/mol.

63. The medical device, polyurethane, or method according to any one of the previous exemplary embodiments, wherein the aliphatic diol comprising a polycarbonate moiety has a weight average molecular weight of at most 1900 g/mol, at most 1800 g/mol, at most 1700 g/mol, at most 1600 g/mol, at most 1500 g/mol, at most 1400 g/mol, at most 1300 g/mol, or at most 1200 g/mol.

64. The medical device, polyurethane, or method according to any one of the preceding exemplary embodiments, wherein the polyurethane comprises at least 30 wt %, at least 35 wt %, at least 40 wt %, at least 45 wt %, or at least 50 wt % of the residue of an aliphatic diol comprising a polycarbonate moiety, based on the total weight of the polyurethane.

65. The medical device, polyurethane, or method according to any one of the preceding exemplary embodiments, wherein the polyurethane comprises at most 70 wt %, at most 65 wt %, at most 60 wt %, or at most 55 wt % of the residue of aliphatic diol comprising a polycarbonate moiety, based on the total weight of the polyurethane.

66. The medical device, polyurethane, or method according to any one of the previous exemplary embodiments, wherein the aliphatic diol comprising a polycarbonate moiety is present in an amount of at least 30 wt %, at least 35 wt %, at least 40 wt %, at least 45 wt %, or at least 50 wt %, based on the total weight of the composition.

67. The medical device, polyurethane, or method according to any one of the previous exemplary embodiments, wherein the aliphatic diol comprising a polycarbonate moiety is present in an amount of at most 70 wt %, at most 65 wt %, at most 60 wt %, or at most 55 wt %, based on the total weight of the composition.

68. The medical device, polyurethane, or method according to any one of the previous exemplary embodiments, wherein the aliphatic diol comprising a polycarbonate moiety has a weight average molecular weight that is no more than 250 g/mol, no more than 200 g/mol, no more than 150 g/mol, no more than 100 g/mol, or no more than 50 g/mol different than the weight average molecular weight of the aliphatic diol comprising a poly(ethylene oxide) moiety.

69. The medical device, polyurethane, or method according to any one of the preceding exemplary embodiments, wherein the chain extender has a molecular weight of at least 60 g/mol, at least 70 g/mol, at least 80 g/mol, at least 90 g/mol, or at least 100 g/mol.

70. The medical device, polyurethane, or method according to any one of the preceding exemplary embodiments, wherein the chain extender has a molecular weight of at most 500 g/mol, at most from 400 g/mol, at most 300 g/mol, at most 200 g/mol, or at most 150 g/mol.

71. The medical device, polyurethane, or method according to any one of the preceding exemplary embodiments, wherein the chain extender comprises ethylene glycol, diethylene glycol, propylene glycol, dipropylene glycol, 1,3-propanediol, 1,4-butanediol, 1,5-pentanediol, 1,6-hexanediol, or 1,8-octanediol.

72. The medical device, polyurethane, or method according to any one of the preceding exemplary embodiments, wherein the chain extender consists of ethylene glycol, diethylene glycol, propylene glycol, dipropylene glycol, 1,3-propanediol, 1,4-butanediol, 1,5-pentanediol, 1,6-hexanediol, or 1,8-octanediol, or a mixture thereof.

73. The medical device, polyurethane, or method according to any one of the preceding exemplary embodiments, wherein the chain extender consists of 1,4-butanediol, 1,6-hexanediol, or a mixture thereof.

74. The medical device, polyurethane, or method according to any one of the preceding exemplary embodiments, wherein the polyurethane comprises at least 1 wt %, at least 2 wt %, at least 3 wt %, at least 4 wt %, or at least 5 wt % of the residue of a chain extender, based on the total weight of the polyurethane.

75. The medical device, polyurethane, or method according to any one of the preceding exemplary embodiments, wherein the polyurethane comprises at most 12 wt %, at most 10 wt %, at most 9 wt %, at most 8 wt %, at most 7 wt %, or at most 6 wt %, of the residue of a chain extender, based on the total weight of the polyurethane.

76. The medical device, polyurethane, or method according to any one of the preceding exemplary embodiments, wherein the composition comprises at least 1 wt %, at least 2 wt %, at least 3 wt %, at least 4 wt %, or at least 5 wt % of the chain extender, based on the total weight of the composition.

77. The medical device, polyurethane, or method according to any one of the preceding exemplary embodiments, wherein the composition comprises at most 12 wt %, at most 10 wt %, at most 9 wt %, at most 8 wt %, at most 7 wt %, or at most 6 wt %, of a chain extender, based on the total weight of the composition.

78. The medical device, polyurethane, or method according to any one of the previous exemplary embodiments, wherein the polyurethane is substantially devoid of silicone.

79. The medical device, polyurethane, or method according to any one of the previous exemplary embodiments, wherein the composition is devoid of silicone.

80. The medical device, polyurethane, or method according to any one of the previous exemplary embodiments, wherein the composition is devoid of silicone-containing moieties.

81. The medical device, polyurethane, or method according to any one of the previous exemplary embodiments, wherein the composition is substantially devoid of silicone-containing moieties.

82. The medical device, polyurethane, or method according to any one of the previous exemplary embodiments, wherein the composition comprises less than 0.1 wt % of silicone-containing moieties, based on the total weight of the composition.

83. The medical device, polyurethane, or method according to any one of the previous exemplary embodiments, wherein the polyurethane is devoid of endgroups.

84. The medical device, polyurethane, or method according to any one of the previous exemplary embodiments, wherein the polyurethane is substantially devoid of endgroups.

85. The medical device, polyurethane, or method according to any one of the previous exemplary embodiments, wherein the polyurethane comprises less than 0.1 wt % of endgroups, based on the total weight of the composition.

86. The medical device, polyurethane, or method according to any one of the previous exemplary embodiments, wherein the polyurethane is linear.

87. The medical device, polyurethane, or method according to any one of the previous exemplary embodiments, wherein the polyurethane is branched.

88. A polyurethane formed from the method of any one of the previous exemplary embodiments.

89. A medical device comprising a polyurethane formed by the method of any one of the previous exemplary embodiments.

90. A medical device comprising the polyurethane according to any one of the previous exemplary embodiments and a bioactive agent.

91. A method of forming a medical device comprising the step of extruding at least a portion of a medical device from a melt comprising the polyurethane according to any one of the previous exemplary embodiments and a bioactive agent.

92. The method or medical device according to any one of the previous exemplary embodiments, wherein the bioactive agent is dispersed in the polyurethane.

93. The method or medical device according to any one of the previous exemplary embodiments, wherein the bioactive agent is solubilized in the polyurethane.

94. The method or medical device according to any one of the previous exemplary embodiments, wherein the amount of bioactive agent in the polyurethane exceeds the solubility limit of the drug in the polyurethane.

95. The method or medical device according to any one of the previous exemplary embodiments, wherein the bioactive agent has a melting temperature that is higher than the melting temperature of the polyurethane.

96. The method or medical device according to any one of the previous exemplary embodiments, wherein the bioactive agent has a melting temperature of from 150° C. to 200° C.

97. The medical device according to any one of the previous exemplary embodiments, wherein the medical device is devoid of catalyst.

98. The medical device according to any one of the previous exemplary embodiments, wherein the medical device is substantially devoid of catalyst.

99. The medical device according to any one of the previous exemplary embodiments, wherein the medical device is in the shape of a rod, tube or ring.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain optional features are described as embodiments of the invention, the description is meant to encompass and specifically disclose all combinations of these embodiments unless specifically indicated otherwise or physically impossible.

The invention claimed is:

1. A medical device comprising:
   (a) a polyurethane comprising the residues of:
      (i) an aliphatic diisocyanate,
      (ii) an aliphatic diol comprising a poly(ethylene oxide) moiety,
      (iii) an aliphatic diol comprising a polycarbonate moiety, and
      (iv) a chain extender; and
   (b) a bioactive agent,
   wherein the polyurethane has a melting temperature offset ($T_m$ Offset) of from 95° C. to 140° C. and has a weight average molecular weight of from 100,000 to 500,000 g/mol.

2. The medical device according to claim 1, wherein the polyurethane is formed by reactive extrusion polymerization of a composition comprising:
   (i) a pre-polymer formed by polymerizing a pre-polymer composition comprising:
      (1) an aliphatic diisocyanate,
      (2) an aliphatic diol comprising a poly(ethylene oxide) moiety, and
      (3) an aliphatic diol comprising a polycarbonate moiety, and
   (ii) a chain extender,
   wherein the composition is devoid of catalyst.

3. The medical device according to claim 2, wherein the polyurethane has been post-cured after the reactive extrusion polymerization at a temperature of from 55° C. to 90° C.

4. The medical device according to claim 3, wherein the duration of post-curing is at least 48 hours.

5. The medical device according to claim 1, wherein the polyurethane has a melting temperature offset ($T_m$ Offset) of from 110° C. to 130° C.

6. The medical device according to claim 1, wherein the polyurethane has a melting temperature onset ($T_m$ Onset) of from 60° C. to 85° C.

7. The medical device according to claim 5, wherein the polyurethane has a melting temperature onset ($T_m$ Onset) of from 60° C. to 85° C.

8. The medical device according to claim 1, wherein the polyurethane has a weight average molecular weight of at least 150,000 g/mol.

9. The medical device according to claim 1, wherein the polyurethane is biostable.

10. The medical device according to claim 1, wherein the polyurethane comprises:

(i) from 20 wt % to 45 wt % of the residue of an aliphatic diisocyanate, (ii) from 3 wt % to 15 wt % of the residue of an aliphatic diol comprising a poly(ethylene oxide) moiety, (iii) from 30 wt % to 70 wt % of the residue of aliphatic diol comprising a polycarbonate moiety, and (iv) from 1 wt % to 10 wt % of the residue of a chain extender, wherein the amounts are based on the total weight of the polyurethane.

11. The medical device according to claim 1, wherein the polyurethane consists of:

(i) from 20 wt % to 45 wt % of the residue of an aliphatic diisocyanate, (ii) from 3 wt % to 15 wt % of the residue of an aliphatic diol comprising a poly(ethylene oxide) moiety, (iii) from 30 wt % to 70 wt % of the residue of aliphatic diol comprising a polycarbonate moiety, and (iv) from 1 wt % to 10 wt % of the residue of a chain extender, wherein the amounts are based on the total weight of the polyurethane.

12. The medical device according to claim 1, wherein the aliphatic diol comprising a poly(ethylene oxide) moiety has a weight average molecular weight of from 500 to 2000 g/mol.

13. The medical device according to claim 1, wherein the aliphatic diol comprising a polycarbonate moiety has a weight average molecular weight of from 500 to 2000 g/mol.

14. The medical device according to claim 1, wherein the polyurethane is devoid of silicone.

15. The medical device according to claim 1, wherein the amount of bioactive agent in the polyurethane exceeds the solubility limit of the bioactive agent in the polyurethane.

16. The medical device according to claim 1, wherein the bioactive agent has a melting temperature that is higher than the melting temperature of the polyurethane.

17. The medical device according to claim 1, wherein the bioactive agent has a melting temperature of from 150° C. to 200° C.

18. The medical device according to claim 1, wherein the medical device is devoid of catalyst.

\* \* \* \* \*